(12) United States Patent
Wong

(10) Patent No.: US 11,357,589 B2
(45) Date of Patent: Jun. 14, 2022

(54) DEVICE FOR CONTROLLING AND LIMITING THERMAL INJURY TO TISSUE DURING THERMAL PROCEDURES WHERE TISSUE IS SIMULTANEOUSLY MECHANICALLY DEFORMED

(71) Applicant: THE REGENTS OF THE UNIVERSITY OF CALIFORNIA, Oakland, CA (US)

(72) Inventor: Brian Jet-Fei Wong, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 16/432,318

(22) Filed: Jun. 5, 2019

(65) Prior Publication Data
US 2019/0365496 A1 Dec. 5, 2019

Related U.S. Application Data

(60) Provisional application No. 62/680,949, filed on Jun. 5, 2018.

(51) Int. Cl.
*A61B 90/00* (2016.01)
*A61B 18/02* (2006.01)
(Continued)

(52) U.S. Cl.
CPC .......... *A61B 90/04* (2016.02); *A61B 18/0218* (2013.01); *A61B 18/24* (2013.01);
(Continued)

(58) Field of Classification Search
CPC ..... A61B 90/04; A61B 17/29; A61B 18/0218; A61B 2018/0212; A61B 2018/00327;
(Continued)

(56) References Cited

U.S. PATENT DOCUMENTS 7,101,365 B1 * 9/2006 Sharon ................ A61B 18/203
606/9
7,131,969 B1 * 11/2006 Hovda ............... A61B 18/1485
606/45
(Continued)

FOREIGN PATENT DOCUMENTS

WO 2006055286 A2 5/2006

OTHER PUBLICATIONS

Office action dated Jul. 28, 2021 in U.S. Appl. No. 16/431,055.

*Primary Examiner* — Carl H Layno
*Assistant Examiner* — Aya Ziad Bakkar
(74) *Attorney, Agent, or Firm* — Shimokaji IP

(57) ABSTRACT

The illustrated embodiments include an apparatus to reduce or eliminate full thickness injury in tissue and to deform tissue which includes a probe or mechanism for deforming tissue, and a subsystem for selectively cooling and/or heating tissue while deformation is of the tissue is being performed. The illustrated embodiments of the invention also extend to a method to reduce or eliminate full thickness injury in tissue and to deform tissue including the steps of deforming tissue, and selectively cooling and/or heating tissue while deformation of the tissue is being performed.

13 Claims, 20 Drawing Sheets

(51) Int. Cl.
*A61B 18/00* (2006.01)
*A61B 17/00* (2006.01)
*A61B 17/29* (2006.01)
*A61B 18/24* (2006.01)

(52) U.S. Cl.
CPC ..... *A61B 17/29* (2013.01); *A61B 2017/00057* (2013.01); *A61B 2018/00023* (2013.01); *A61B 2018/00327* (2013.01); *A61B 2018/00642* (2013.01); *A61B 2018/00714* (2013.01); *A61B 2018/00791* (2013.01); *A61B 2018/0212* (2013.01); *A61B 2090/049* (2016.02); *A61B 2090/0418* (2016.02); *A61B 2090/0463* (2016.02)

(58) Field of Classification Search
CPC ...... A61B 2090/0463; A61B 2090/049; A61B 2018/00714; A61B 2018/00791; A61B 2017/00057; A61N 2005/0668
See application file for complete search history.

(56) References Cited

U.S. PATENT DOCUMENTS

| | | | |
|---|---|---|---|
| 2006/0195073 A1 | 8/2006 | Connors | |
| 2012/0323232 A1* | 12/2012 | Wolf | A61B 18/02 606/33 |
| 2016/0287334 A1 | 10/2016 | Monteris | |
| 2017/0231651 A1* | 8/2017 | Dinger | A61B 18/1445 604/20 |

* cited by examiner

Sapphire Cooling

Goal: Preserve the nasal mucosa while creating thermal injury to the underlying cartilage tissue

FIG. 6A

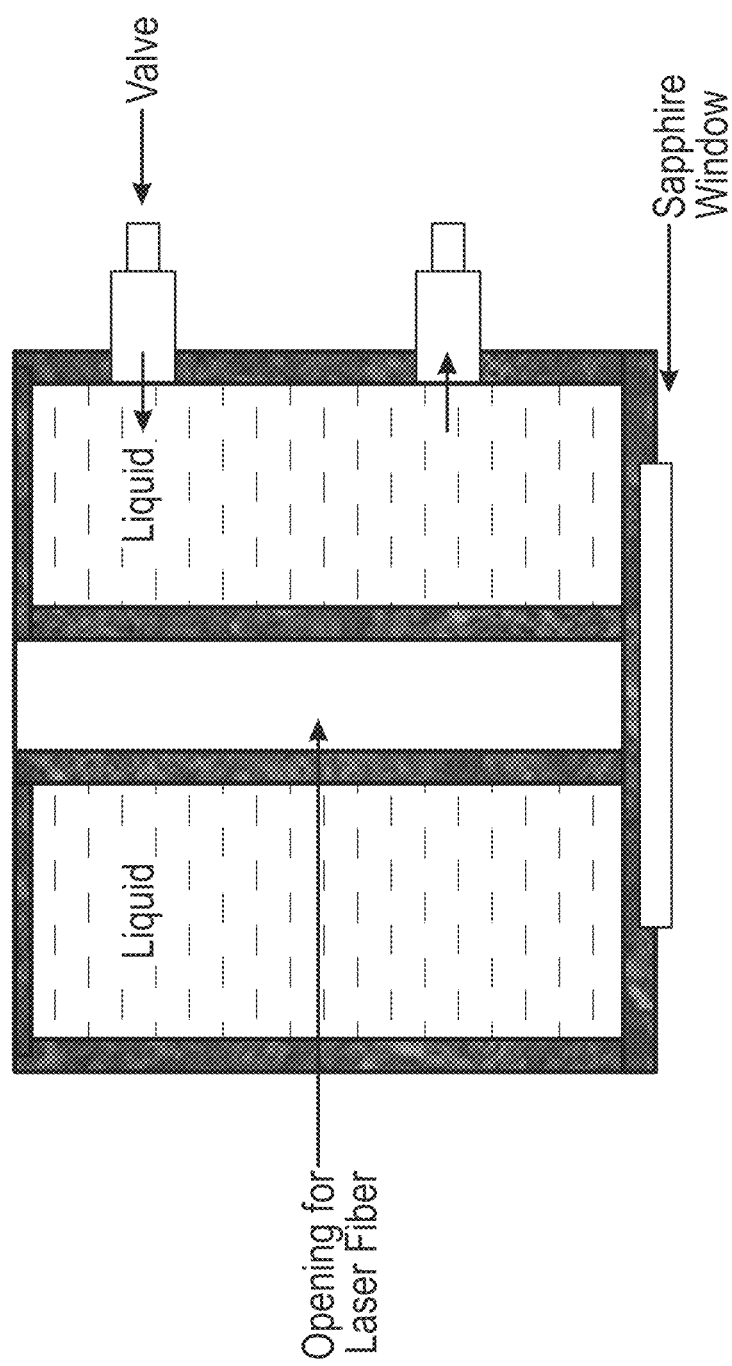

First Experiment-
Surface Cooling Measurements

FIG. 6G

Note on how test was run:

1) Placed thermocouple on surface,
2) started temperature measurements
3) placed a drop of chilled saline on thermocouple and tissue surface
4) move tissue under the sapphire
5) lower sapphire onto tissue and allow time for cooling From looking at the graph Steps 1-3 correlates with 0-5 seconds Step 4 correlates with 5-15 seconds Step 5 correlates with 15-180 seconds

FIG. 6J

Second Experiment-
Temperature measurements at three tissue regions
(surface, 2mm, 4mm)

FIG. 6K

Refined Experiment Technique

FIG. 6L

DEVICE FOR CONTROLLING AND LIMITING THERMAL INJURY TO TISSUE DURING THERMAL PROCEDURES WHERE TISSUE IS SIMULTANEOUSLY MECHANICALLY DEFORMED

CROSS REFERENCE TO RELATED APPLICATIONS

This application claims the benefit of and priority to U.S. provisional application No. 62/680,949, filed Jun. 5, 2018, which is incorporated herein by reference.

BACKGROUND OF THE INVENTION

The present invention generally relates to the field of tissue reconstruction and, in particular, to thermo-plastically forming tissue and cartilage in particular.

Cartilage serves many functional and structural roles in the head and neck, including the support of soft tissue in the ear and nose, maintenance of airway patency, phonation, and joint movement. The functional and esthetic defects in the head and neck that result from cancer surgery, trauma, or congenital malformations have led to the development of surgical techniques to reshape cartilage to recreate damaged or absent structures.

Conventional reconstructive techniques (e.g., otoplasty, rhinoplasty, tracheoplasty) involve the grafting or shape modification of autologous cartilage (harvested from the ear, nasal septum, or rib). Currently, the graft is carved, sutured, and/or morselized to recreate the shape of the absent tissue and, as a consequence, abundant normal healthy cartilage tissue is discarded. These techniques also in general require surgical exposure of the tissue to provide direct access to the graft tissue. Further manipulation of tissue in this fashion creates focal injury to the extracellular matrix. Because only a limited amount of cartilage is available from donor sites, conventional reconstructive techniques may lead to significant donor site morbidity. Similarly, some cartilaginous malformations in the head and neck are treated using surgical techniques that do not require grafting (e.g., rhinoplasty, laryngoplasty), but rather reshaping pre-existing cartilage structures in situ using the aforementioned traditional reconstructive techniques. These techniques have the same limitations as grafting techniques, and also require open/invasive (non-endoscopic) surgical approaches that frequently result in undesirable, irreversible tissue changes and complications that may require revision surgery, and possibly additional cartilage grafting.

Current reconstructive techniques include carving, morselizing, scoring, or suturing native cartilage grafts. The disadvantages of these approaches include donor site morbidity from graft harvest, waste of excess graft tissue, shape memory effects, and lack of control over warping, particularly in costal cartilage tissue.

Several alternative approaches to reshaping cartilage have been advocated, including enzymatic digestion in situ, radiofrequency (RF) reshaping, and laser cartilage reshaping. Of these approaches to changing the shape of native cartilage tissue, laser reshaping has received the most attention. In 1993, Helidonis et al. "Laser Shaping Of Composite Cartilage Grafts". Am J Otolaryngol 1993; 14: 410-412, proposed an alternative laser assisted approach based on thermal-mediated stress relaxation to reshape cartilage. Despite clinical uses of laser technology to reshape human cartilage, this method remains investigational, and the associated biophysical changes accompanying shape change are incompletely understood.

Recently, several new techniques have been developed and/or investigated including electroforming, thermoforming (laser and RF), and enzymatic reshaping. In each of these cases, the intrinsic forces in tissue which resist deformation are relieved or balanced by accelerating stress relaxation, albeit the molecular mechanisms of action may be different in each case.

Various thermal techniques are also under development that generate heat in the nasal septum. One concern related to these procedures is that heating the septum or its component structures (e.g., cartilage, bone, mucous membrane, perichondrium, blood vessel) will result in full thickness injury to the nasal structures.

SUMMARY OF THE INVENTION

The illustrated embodiments include an apparatus to reduce or eliminate full thickness injury in tissue and to deform tissue which includes a probe or mechanism for deforming tissue, and a subsystem for selectively cooling and/or heating tissue while deformation is of the tissue is being performed.

In one aspect of the invention, an apparatus to reduce or eliminate full thickness injury in tissue and to deform tissue comprises means for deforming tissue; and means for selectively cooling and/or heating tissue while deformation of the tissue is being performed.

In another aspect of the invention, a method to reduce or eliminate full thickness injury in tissue and to deform tissue comprises deforming tissue; and selectively cooling and/or heating tissue while deformation of the tissue is being performed.

In a further aspect of the invention, a system to treat tissue comprises a device configured for insertion into a human body cavity; a heat source in communication with the device; a cooling source in communication with the device; a temperature sensor configured to sense temperature of the tissue; and a controller in communication with the heat source, cooling source, and the temperature sensor.

In yet another aspect of the invention, a probe to treat a nasal septum comprises an end piece configured to: contact a surface of the nasal septum; communicate with a laser source; communicate with a cooling source; an optic fiber between the end piece and the laser source; a shaft connected to the end piece; and a flow tube, in the shaft, that extends between the cooling source and the end piece.

The tissue may include a nasal septum and the subsystem for selectively cooling and/or heating tissue may heat selected tissue portions, while simultaneously cooling other tissue portions to avoid or minimize tissue damage.

The probe for deforming and the subsystem for selectively cooling and/or heating comprises a multisided device for insertion into each nasal fossa, the device having two corresponding arms, each in contact with different sides of the nasal septum, where the arm in contact with the side of the nasal septum opposite the side of the nasal septum to be treated includes means to be cooled to a temperature below ambient or body temperature.

The probe can include an endpiece, and the subsystem for selectively cooling and/or heating tissue can include a laser and optics for delivering mediating light energy to the endpiece of the probe, a cooling subsystem communicating through the probe to the endpiece, a temperature sensor thermally coupled to the tissue being treated, a servomechanism or microprocessor controller coupled to cooling subsystem, the laser, and to the temperature sensor to provide selectively controlled heating and cooling to the tissue to be treated.

The probe can have two arms, wherein one arm is provided with a subsystem for selectively heating the tissue to be treated and wherein the other arm is provided with a subsystem for selectively cooling tissues adjacent to the tissue to be treated.

The probe can have two arms, wherein one arm is provided with a subsystem for selectively heating and for selectively cooling the tissue to be treated and wherein the other arm is provided with a subsystem for selectively cooling tissues adjacent to the tissue to be treated.

In another exemplary embodiment, the probe can have two arms and each arm is provided with a subsystem for selectively heating and for selectively cooling the tissue to be treated or the tissues adjacent to the tissue to be treated depending on which arm is position proximate to which tissue.

In still other exemplary embodiments, the probe for deforming tissue and the subsystem for selectively cooling and/or heating tissue means is used to selectively deform, heat and/or cool trachea, ear, larynx, skin, fat, muscle, or cartilage.

The subsystem for selectively cooling and/or heating tissue may comprise a heat sink to cool tissue using heat exchange materials, chilled water flow, thermoelectric cooling, coolant circulation, or cryogen spray.

The subsystem for selectively cooling and/or heating tissue may comprises means for precooling a probe prior to insertion of the probe into the nose or other body orifice.

The subsystem for precooling the probe may cool the probe to a temperature depending upon the heat capacity of the probe, the thickness of the tissue subject to mediation, the mode or method of heat generation in the tissue or in adjacent tissues which are heated, the rate of heat generation in the adjacent tissues, and the rate of cooling of the probe during mediation.

The subsystem for selectively cooling and/or heating tissue may be automatically controlled by a microprocessor.

The probe for deforming tissue can apply a mechanical deformation before or after cooling and heating of the tissue by the subsystem for selectively cooling and/or heating tissue.

The probe for deforming tissue and the subsystem for selectively cooling and/or heating tissue can be included in a device used for otorhinolaryngology, orthopedics, plastic surgery, general surgery, dermatology, and septoplasty operations.

The illustrated exemplary embodiments of the invention may also extend to a method to reduce or eliminate full thickness injury in tissue and to deform tissue, including the steps of deforming tissue, and selectively cooling and/or heating tissue while deformation is of the tissue is being performed.

The tissue may include a nasal septum and the step of selectively cooling and/or heating tissue may heat selected tissue portions, while simultaneously cooling other tissue portions to avoid or minimize tissue damage.

The steps of deforming and selectively cooling and/or heating may include the steps of inserting a multisided device into each nasal fossa, the device having two corresponding arms; contacting with different sides of the nasal septum with one of the two corresponding arms; contacting the side of the nasal septum opposite that side of the nasal septum to be treated to cool the contacted side to a temperature below ambient or body temperature.

The steps of deforming tissue and selectively cooling and/or heating tissue may include the steps of selectively deforming, heating and/or cooling trachea, ear, larynx, skin, fat, muscle, or cartilage.

The step of selectively cooling and/or heating tissue may include the step of precooling a probe prior to insertion of the probe into the nose or other body orifice. The step of precooling the probe may cool the probe to a temperature depending upon the heat capacity of the probe, the thickness of the tissue subject to mediation, the mode or method of heat generation in the tissue or in adjacent tissues which are heated, the rate of heat generation in the adjacent tissues, and the rate of cooling of the probe during mediation.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112, they are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

The illustrated exemplary embodiments can reduce or eliminate full thickness injury to nasal tissues, and also can deform cartilage tissue as well. Thus, an illustrated exemplary embodiment is a device to deform and cool tissue and, in particular, nasal cartilage. This device and inventive concept is used to minimize tissue damage during surgical procedures to the nasal septum that generate heat.

Figure 1:
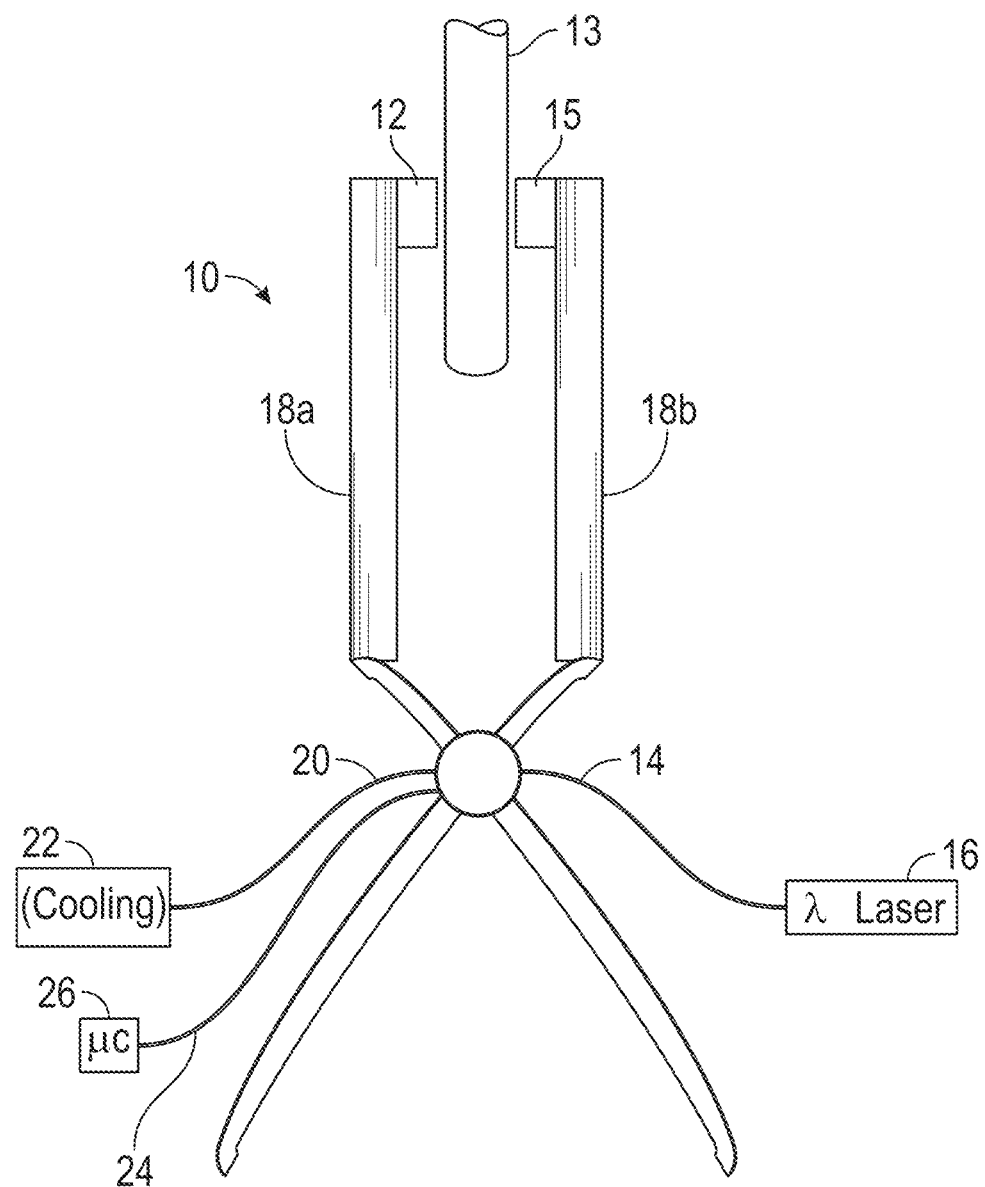
FIG. 1 is a diagram illustrating the elements of a device for practicing the illustrated exemplary embodiment of the invention utilizing two arms.

In FIG. 1, an exemplary embodiment can be comprised of a "tong" or two component device 10 with arms 18a and 18b configured for insertion into both nostrils to allow application of laser energy, cooling, and/or mechanical deformation to both sides of the septum 13. Conceptually, this is bilateral treatment which may be differential. The two halves of this device 10 may be the same or differ in geometry. Each half can operate in the same or different modes: e.g., left cooling only and right cooling plus laser.

The illustrated embodiment is thus directed to a method that includes the steps of disposing a multisided jig, device, tool or instrument 10 (hereinafter referenced as "device") into each nasal fossa. Device 10 can have two arms 18a and 18b. At least one portion of arm 18b of the device 10 is configured to contact the nasal septum 13, and may be cooled to temperatures below ambient or body temperature. The control of temperature of arm 18b of the device 10 can be monitored with a temperature sensor 28 and communicated to a servomechanism within cooling system 22 for providing the coolant to the device 10 or to microprocessor 26 which performs the same function. The illustrated embodiment of the device 10 prevents overheating of the non-treated side of the nasal septum 13 adjacent to arm 18b of device 10 during procedures and operations, which might otherwise heat tissues on the non-treated side.

One of the illustrated embodiments of the device 10 is particularly arranged and configured to simultaneously deform and cool the nasal cartilage. Deformation is combined with a heat sink 15 to cool tissue, which may be maintained at a variety of different temperatures depending upon the application. Cooling can be accomplished through a number of well-known methods, including the use of heat exchange materials, water flow/chilled, thermoelectric, coolant circulation, and cryogen spray. The cooled arm 18b and/or heat sink 15 may even be pre-cooled prior to insertion into the nose or other body orifice.

The rate of cooling can depend upon the thickness of the tissue 19 that needs to be cooled, the mode or method of heat generation on the other side of the tissue 13, and the rate of heat generation. Both the rate of cooling or energy removal and the rate of heat generation may come under the control of microprocessor 26. Cooling with subsequent thaw or return to ambient or body temperature may in itself induce crystallization and subsequent phase changes resulting in tissue shape change. Mechanical deformation may occur before or after cooling and heating of the tissue 13.

Figure 2A:
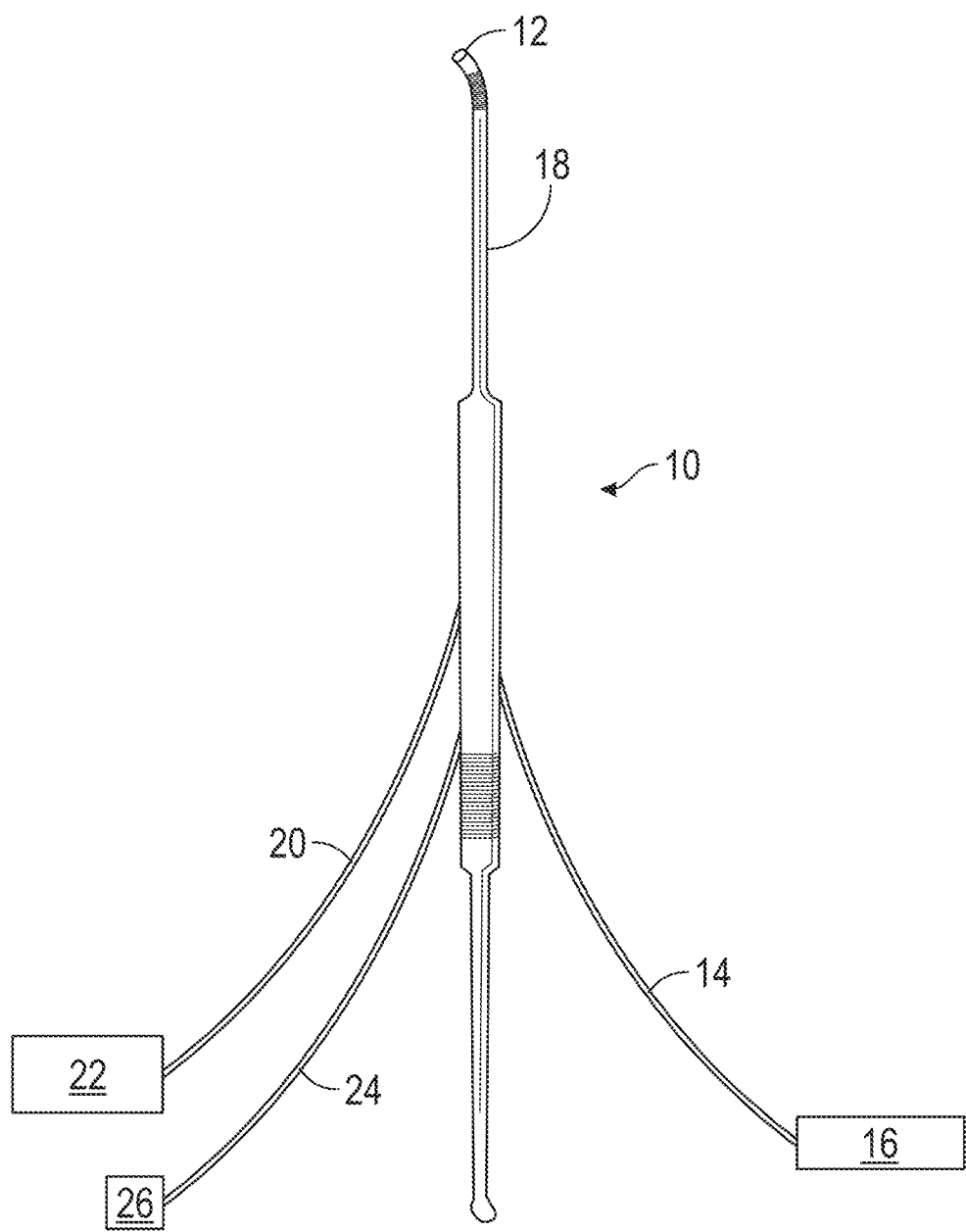
FIGS. 2A-2B are diagrams illustrating the elements of a device for practicing the illustrated exemplary embodiment of the invention utilizing one arm.
Figure 2B:
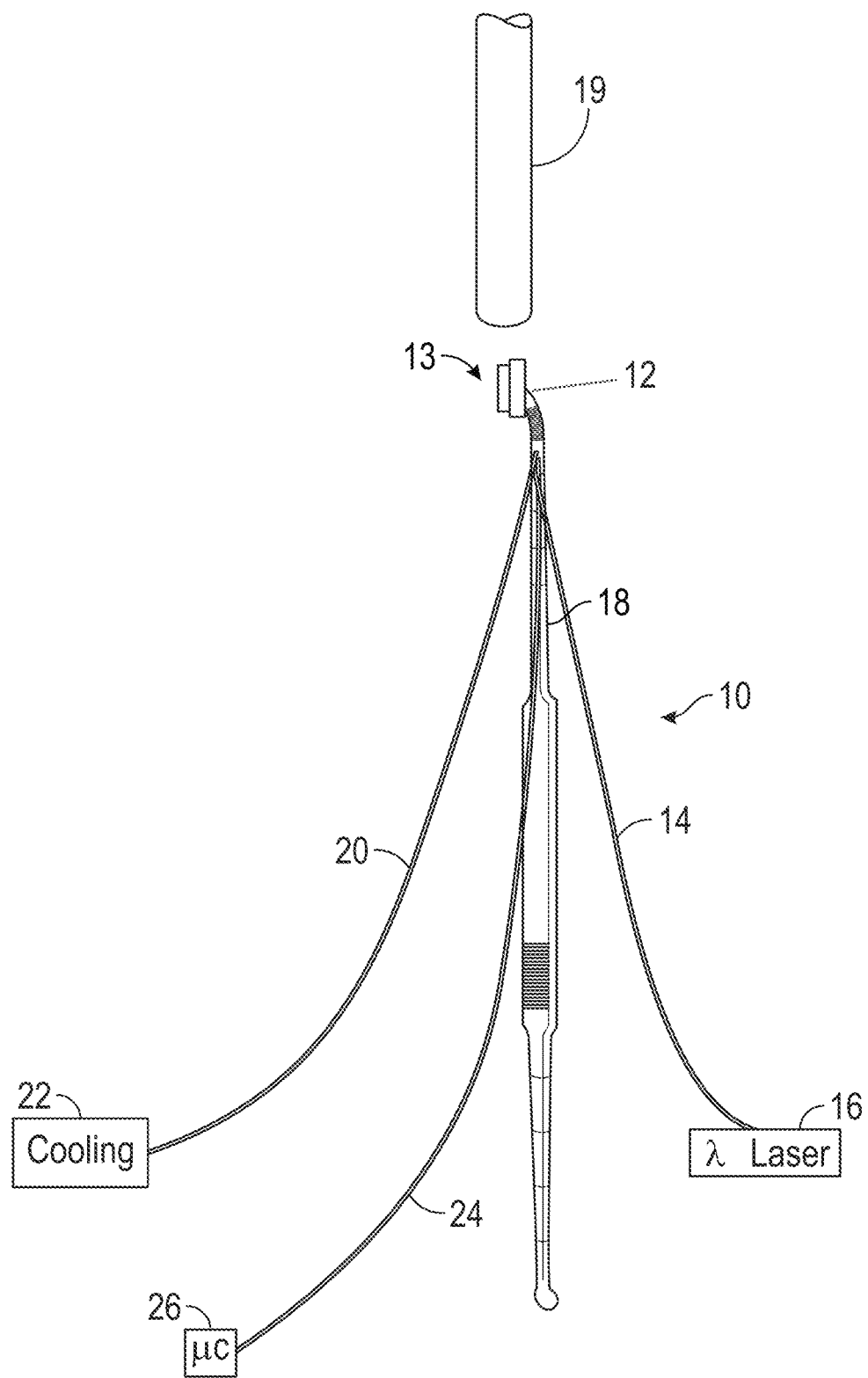

In another exemplary embodiment shown in FIG. 2, illustrated device 10 has the same form or a substantially similar form to a conventional nasal instrument such as a Cottle elevator. Device 10 is long and thin relative to the size of the human nasal structures. It is suitably stiff to allow the physician or user to transmit force to the septum at the region where device 10 is in physical contact with the septum 19. Treatment occurs by moving the device 10 from point to point across the surface of the septum 19. Laser energy can be delivered where deemed necessary by the surgeon. In the illustrated embodiment, a medical laser in the wavelength bands 1.32, 1.45, 1.54, 1.56, 2.1, 10.6 μm, with a power in the range of 1-12 Watts, selectively providing a pulsed or continuous beam can be desirable. The laser energy is provided through an aperture 12 which is coupled by a fiber optic 14 to an external, controllable laser 16.

Mechanical deformation, cooling and delivering of laser energy can be applied simultaneously or one after another. Mechanical deformation and cooling can be applied prior to the laser energy to allow for sufficient cooling of the mucosa.

Figure 3:
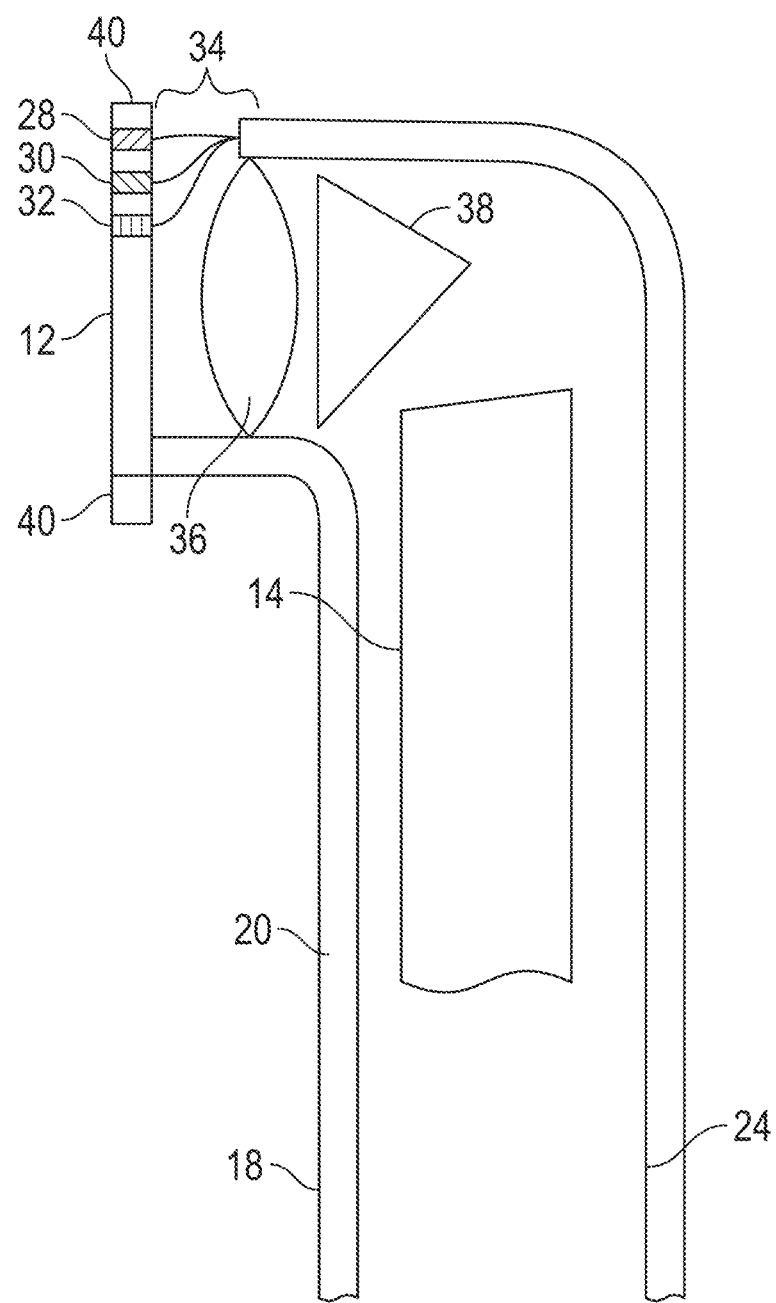
FIG. 3 is a diagram illustrating a cross-sectional view of the distal elements in a probe used in a device according to the illustrated exemplary embodiments.

In FIG. 3, in another exemplary embodiment, the device 10 can be comprised of a small cylindrical or other shaped active end piece 12 that is positioned at or near the terminus of the optical fiber 14 and communicated thereto with appropriate lenses or delivery optics 34. End piece 12 thus may include a sapphire window in contact with tissue, a prism 38 to bend the laser light and a GRIN lens 36 collectively comprising optics 34 to focus the laser beam onto end piece 12. The laser light terminates in end piece 12 which is composed of sapphire or similar optically clear material made of high thermal conductivity. For example, a thermal conductivity in the range of 10-100 W/mK is useful.

Device 10 can include multiple optical, electronic, and hydraulic components, yet is small enough to fit through the nose and not significantly obscure the surgeon's view of the septum 19 or the region of treatment. An exemplary active element or end piece 12 is about 1 cm in diameter. The shaft/handle 18 that connects to the cylindrical head or end piece 12 can have a plurality of ducts or shafts therein to accommodate fluid flow tube 20, laser fiber 14, microcable 24 and any necessary electronics.

In embodiments, the flexible tube 20 communicates end piece 12 through handle 18 with a source 22 of cooling medium, such as safe cooling solutions (salt water for example, or ethylene glycol). Water tight or hermetic seals can be employed to allow direct contact cooling of the sapphire window of end piece 12, which is in contact with the tissue without allowing direct contact between the tissue and the cooling medium.

In embodiments, end piece 12 may include internal lumens defined in the sapphire window to provide an internal cooling heat exchange system. Return flow of the cooling medium is provided through the interior of handle 18 or tube 20 may be provided with a pair of fluid conducting lumens.

All of the components of device 10, and end piece 12 in particular, can be composed nontoxic materials. End piece 12 can be cooled before, after, and/or during laser irradiation. Cooling of the sapphire can be accomplished by circulating chilled fluid around the cylindrical vestibule that holds the lens, fiber and sapphire. The fluid can flow passively, via gravity or by means of a pump. Likewise, dry air under pressure or at high flow rates can be used as well.

End piece 12 can also be provided with one or more sensors 28-32, such as a thermal sensor 28, stress sensor 30, or an optical sensor 32 which uses light scattering measurement techniques to measure tissue parameters and site parameters. The reaction force to the applied deformation tissue can be measured by the stress sensor 30 and monitored by computer 26 through microcable 24. This information can be combined with the specimen thickness to obtain an accurate characterization of the real time mechanical properties of the tissue through computer modeling using computer 26 coupled to sensors 28-32.

The sensors 28-32 are communicated through a data microcable 24 to an analyzer or computer 26. Optic fiber 14, tube 20 and cable 24, in addition to being miniaturized, can be bundled into a single tether between device 10 and the supporting equipment, illustratively shown in FIGS. 1 and 2 to include laser 16, cooling source 22 and computer 26.

The portion of the end piece 12 in physical or thermal contact with tissue may be made as small as the sapphire window included in end piece 12 or as large as desired, by including, for example, a metal frame 40 around the sapphire window to provide for additional cooling and tissue deformation.

In use, end piece 12 with sapphire window can be placed in contact with the septal mucosa and laser energy can be delivered through the window. Sapphire is an economical material, though other suitable materials may be used. The sapphire may be place flushly against the surface of the mucous membrane. The end piece 12, with sapphire window 12*a*, may be concave, convex, cylindrical or have a complex surface shape as shown in FIGS. 4*a*, 4*b*, 4*c* and 4*d* respectively to differentially compress the mucous membrane.

Figure 4D:
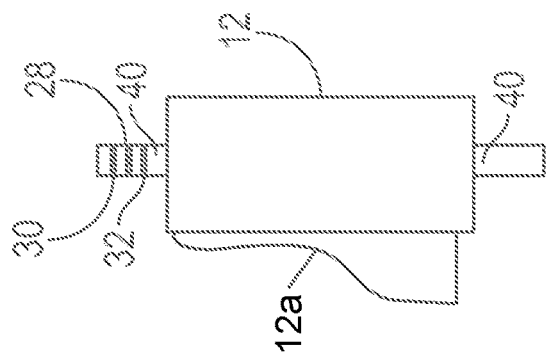
FIGS. 4a-4d are perspective views of an endpiece of the probe of the illustrated embodiments showing a concave, convex, cylindrical, and free form shape for contact with the tissue to be treated.
Figure 4C:
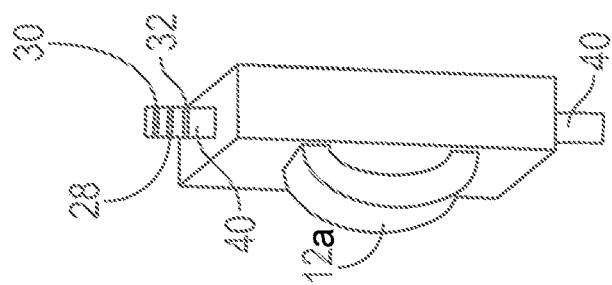
Figure 4B:
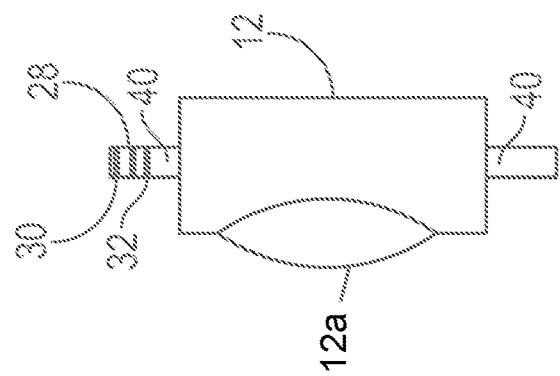
Figure 4A:
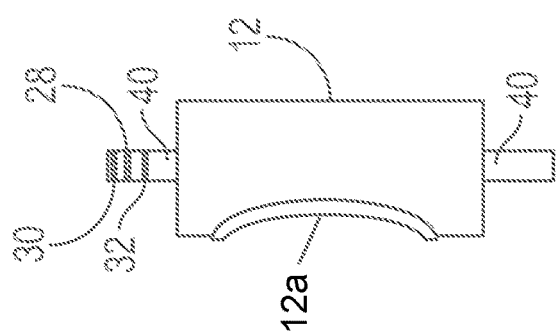

As shown in FIG. 4*d* the sapphire window may have a complex surface shape to both focus/shape light (influence rate distribution) and also differentially compress the mucous membrane. Compression of the tissue may homogenize the optical properties of the tissue leading to more uniform or predictable light distribution in the tissue. Compression removes or reduces impact of blood flow and hemoglobin on the opto-thermal response of tissue. Blood flow can be eliminated transiently if needed. Compression will also change the refractive index locally and differentially.

While a fluid based circulatory heat exchange design included within end piece 12 and source 22 is desirable, other methods of cooling the tissue could be used such as a cryogen spurt delivered within a closed system included with the enclosure of hollow handle 18 with no escape of cryogen to the ambient environment. Cryogen mist or flow can cool the delivery head of end piece 12 with separate entry and exit ports for the cryogen. A thermo-electrical cooling system can be incorporated into the end piece 12 as well.

Figure 5:
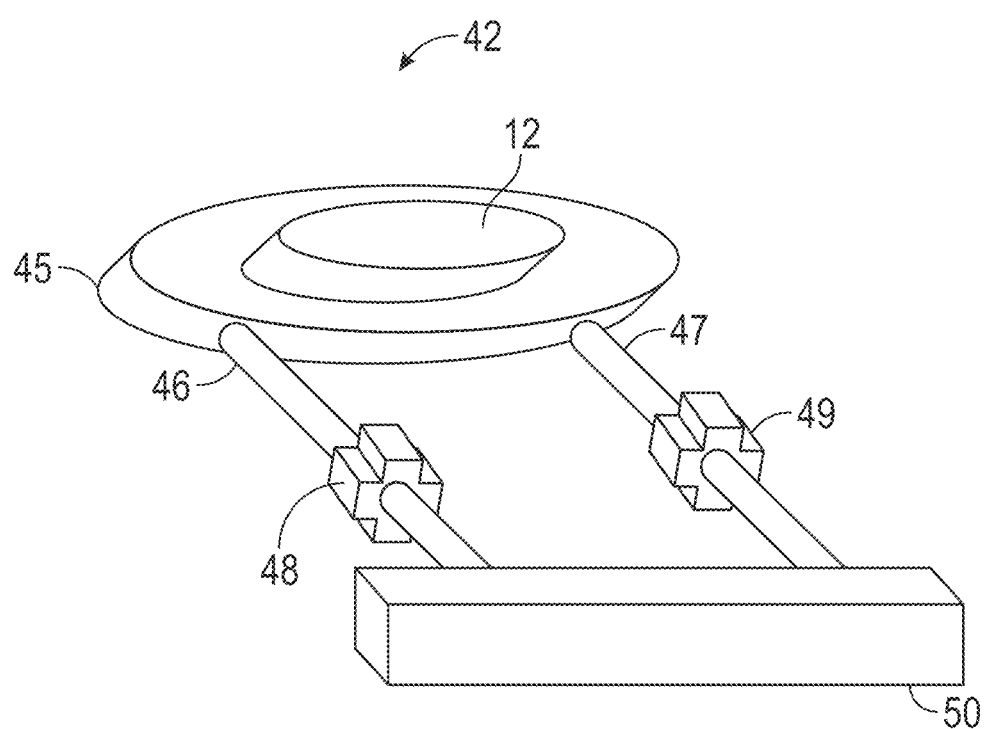
FIG. 5 is a diagram of a pneumatic device for surrounding the endpiece for the purpose of cooling tissue surface to prevent thermal injury.

In FIG. 5, the end piece 12 or sapphire window shaped contact point can be replaced or surrounded by a pneumatic device 42 that is flushed with cooled liquid. Pneumatic device 42 performs the function of cooling tissue surface to prevent thermal injury. The pneumatic device 42 can be comprised of inflatable balloon 45, inflation valve 46, deflation valve 47, inlet tubing 48 and outlet tubing 49 connected to the close circuit liquid or gas circulation system 50. Device 42 can be provided with a toroidal geometry to accommodate light delivery through the center of the toroid. It can be inflated and deflated slowly or quickly by opening and closing inflation and deflation valves. Cooling intensity can be controlled by partial opening and closing of inflation and deflation valves.

Condensation may occur along any point of the optical pathway, and can be compensated for by the use of continuous, intermittent or pulsed deliver of dry air, nitrogen, or other gases.

End piece 12 may be provided with a dynamic aperture 44 for cooling, which changes or controls the delivery of light or cooling fluid to end piece 12 to alter the spatial extent of tissue subject to temperature change. This can be adjusted in real time to alter both the spatial and temporal extent of the delivery of light or cooling fluid. Dynamic aperture 44 is comprised of an iris mounted within end piece 12 on the optical axis of the optical system.

One alternate approach is to use a very large device 10 that would cover a great surface area and perform comprehensive modification of the septum over a large region of interest.

Another variation is the use of steady state cooling and pulsatile cooling of the septum 19.

A pattern of irradiation with device 10 through end piece 12 can be arranged and configured to be pointwise, linear, or geographic over an entire region of interest of arbitrary size and pattern depending on the size and shape of end piece 12.

Device 10 may also incorporate technology such as ultrasound to determine the thickness of the mucous membranes and cartilage. This information can be used in real time by computer 26 to optimize or individualize therapy.

The illustrated embodiments of the device 10 can also be used in other organs where deformation and cooling is required such as trachea, ear, larynx skin, fat, and muscle. The illustrated embodiments of the device 10 have use in the optimization of many surgical procedures in particular those in the nose and upper airway that require control and optimization of heat generation or removal of heat. The illustrated embodiments of the invention may be useful for otorhinolaryngology, orthopedics, plastic surgery, general surgery, and dermatology procedures in the body. A desired application may be for use in septoplasty operations.

EXAMPLES

Figure 6B:
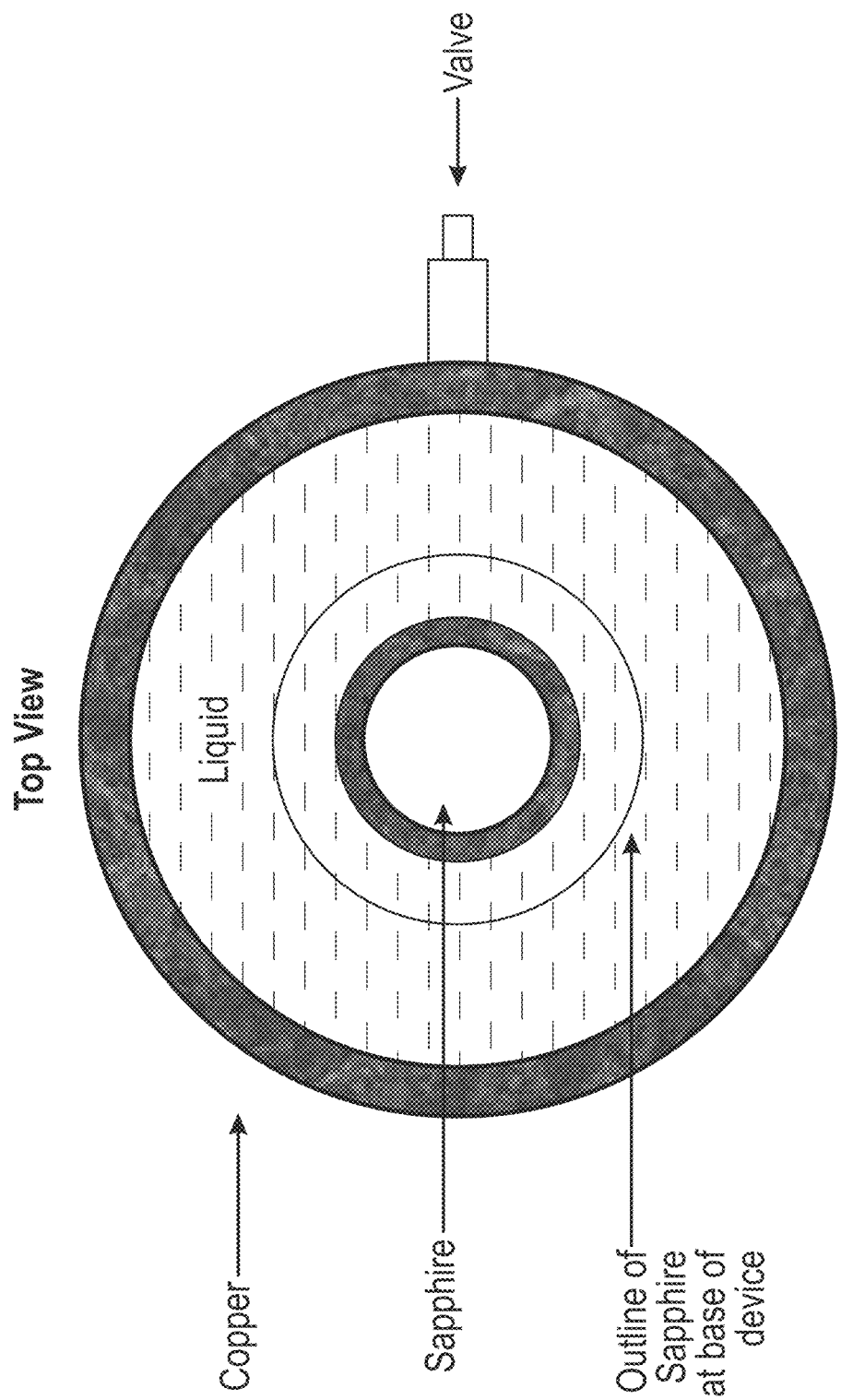
FIGS. 6A-6N are a series of diagrams depicting examples of embodiments of the present invention.
Figure 6D:
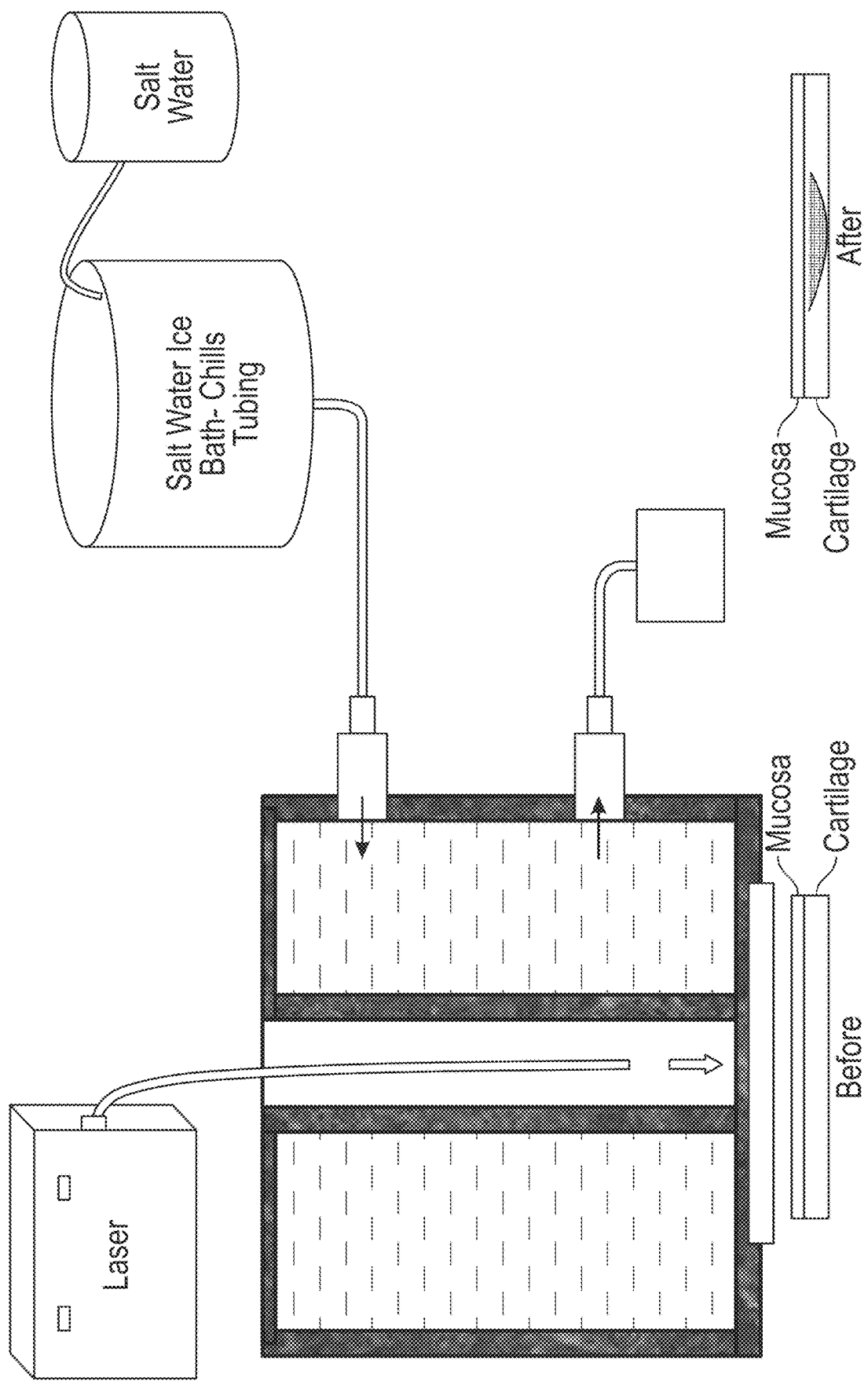
Figure 6E:
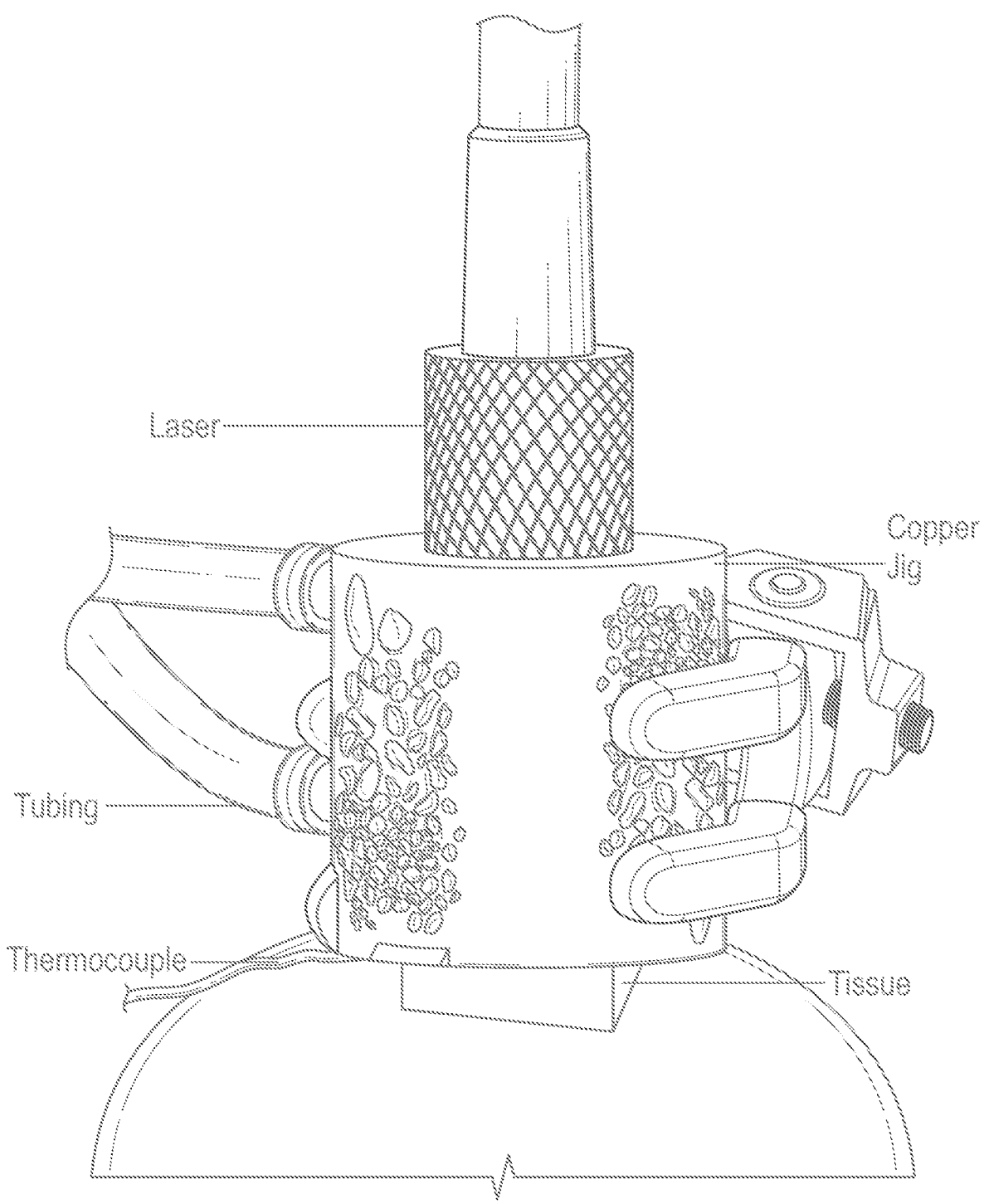
Figure 6F:
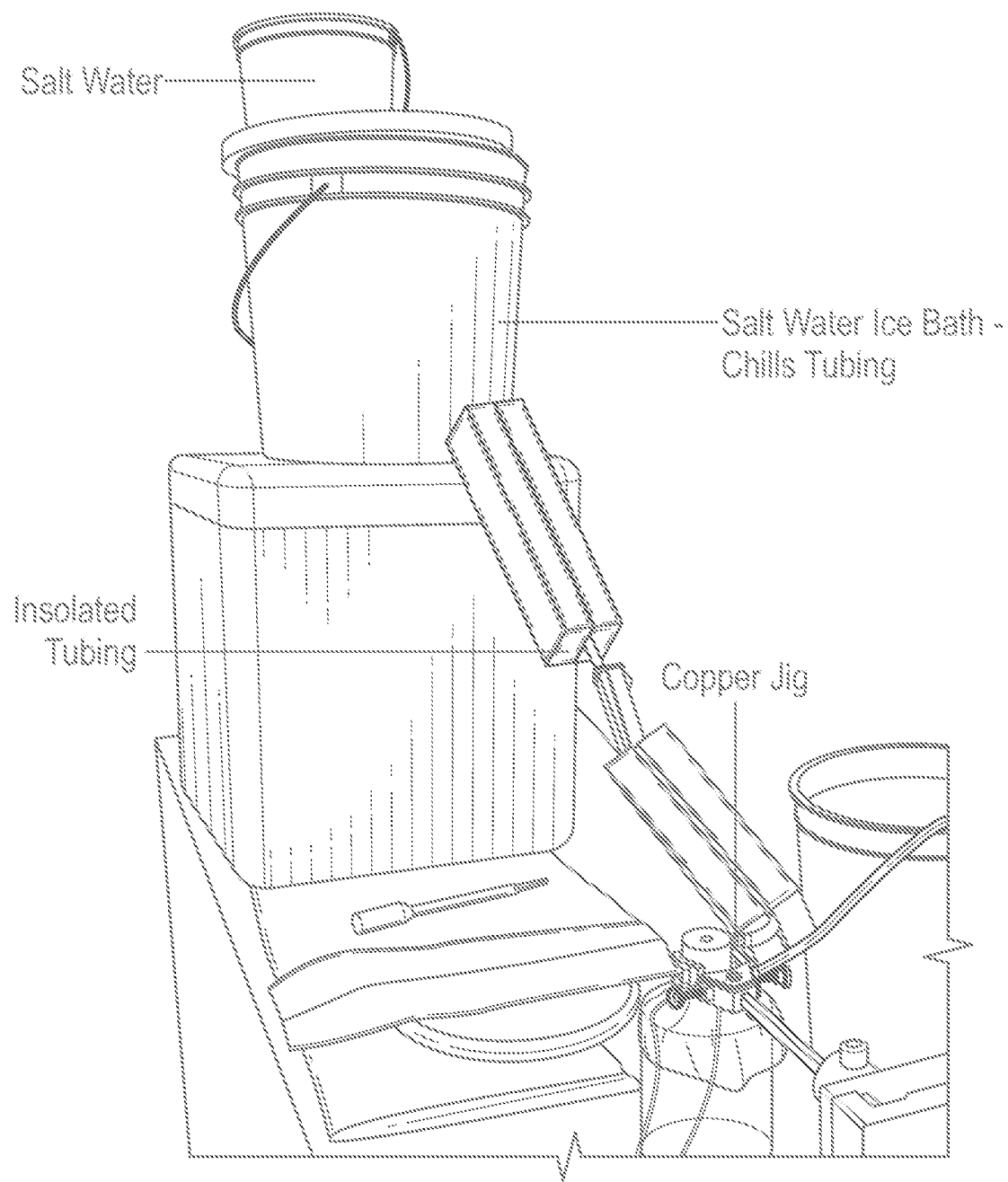
Figure 6H:
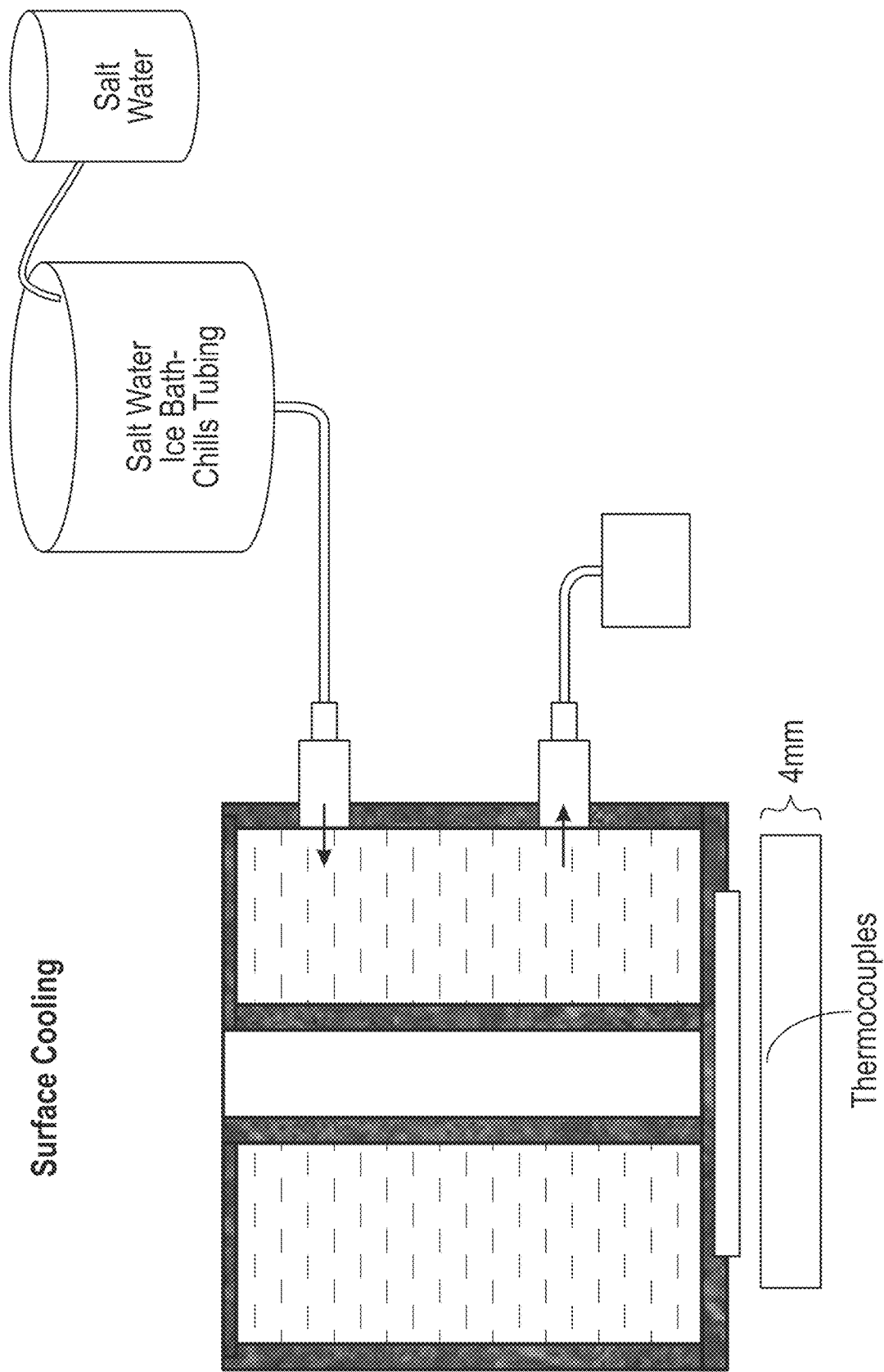
Figure 6I:
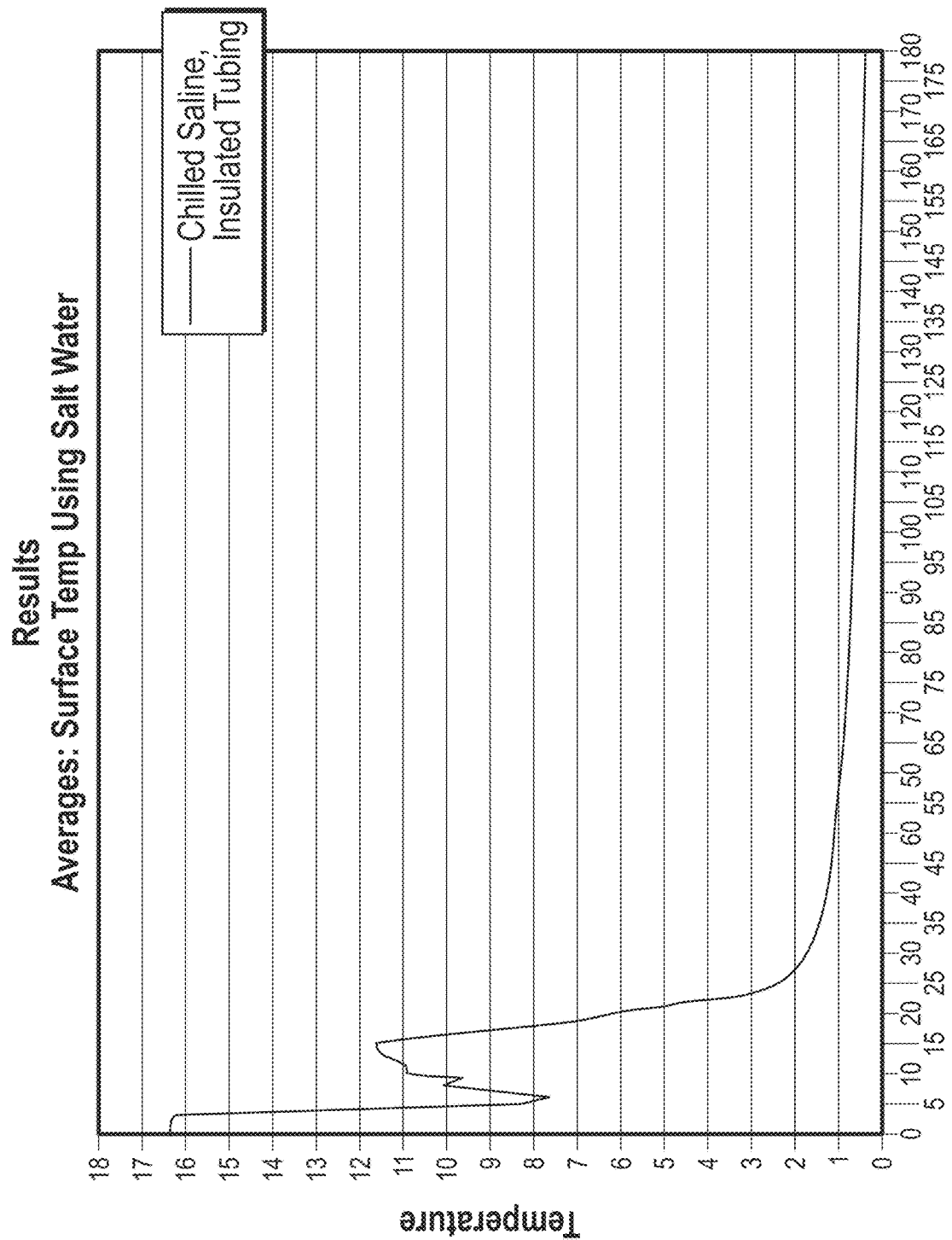
Figure 6M:
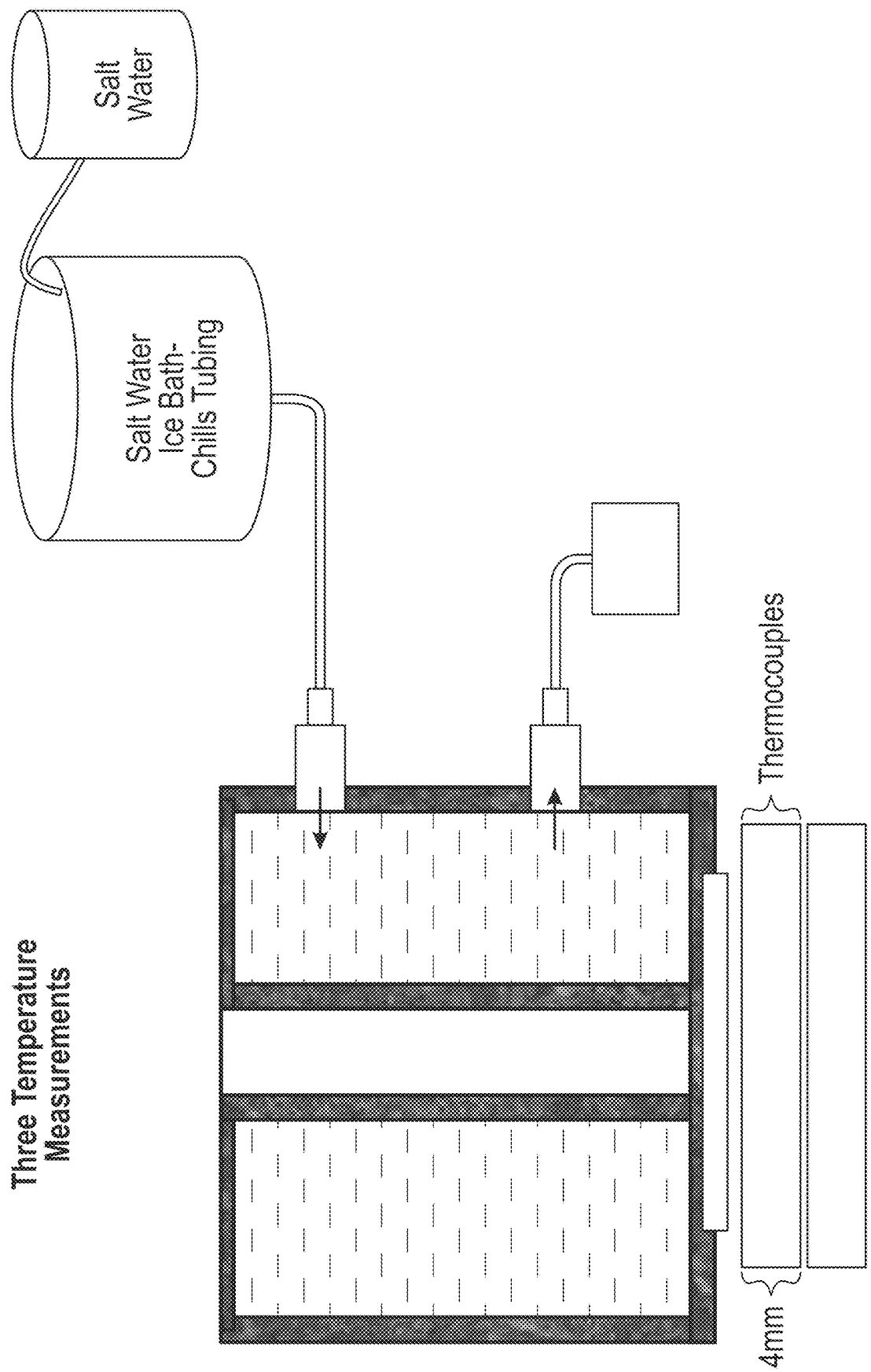
Figure 6N:
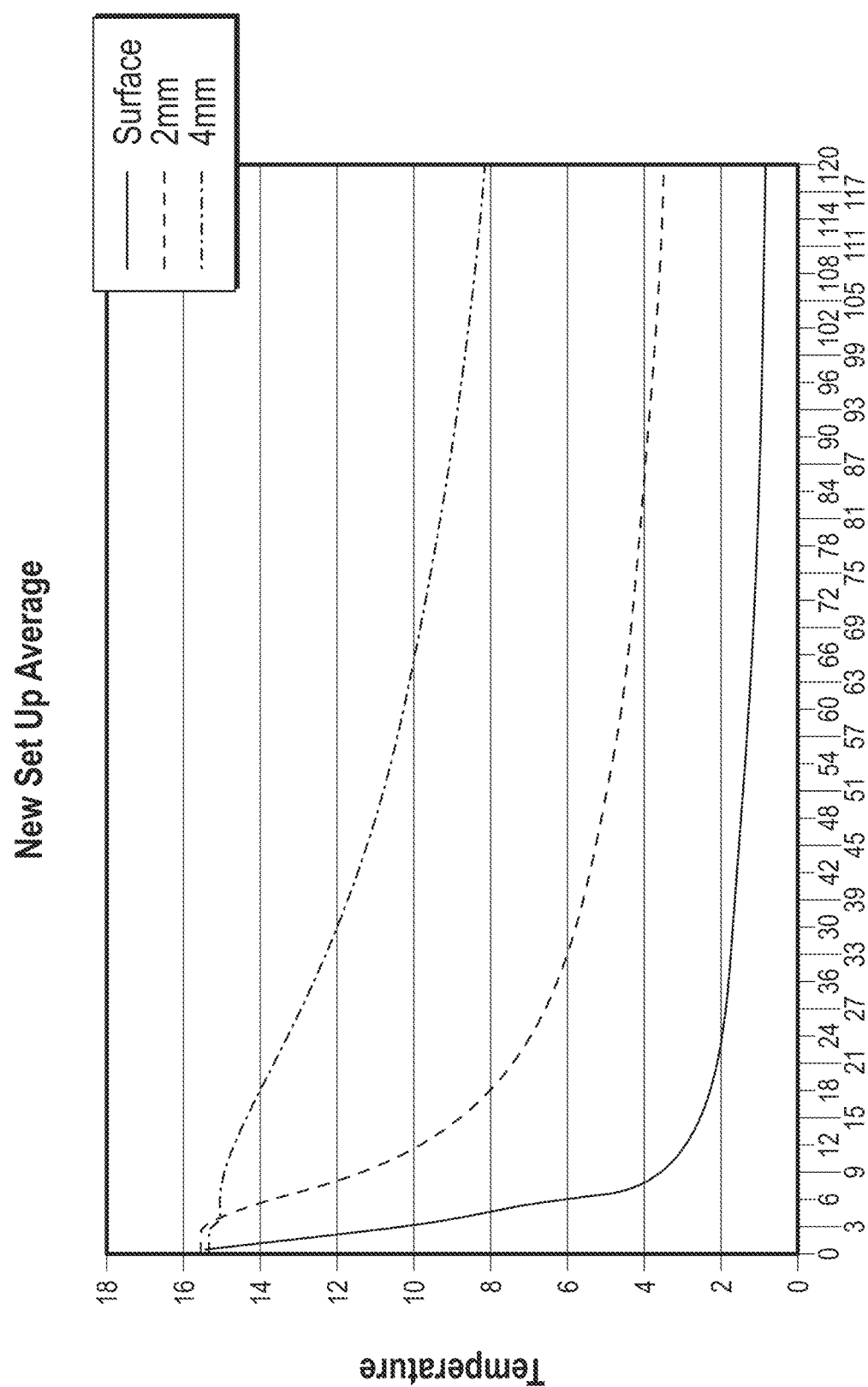

FIGS. 6A-6N are a series of fourteen diagrams depicting exemplary embodiments of the present invention.

Many alterations and modifications may be made by those having ordinary skill in the art without departing from the spirit and scope of the embodiments. Therefore, it must be understood that the illustrated embodiments have been set forth only for the purposes of example and that it should not be taken as limiting the embodiments as defined by the following embodiments and its various embodiments.

Therefore, it must be understood that the illustrated embodiments have been set forth only for the purposes of example and that it should not be taken as limiting the embodiments as defined by the following claims. For example, notwithstanding the fact that the elements of a claim are set forth below in a certain combination, it must be expressly understood that the embodiments include other combinations of fewer, more or different elements, which are illustrated embodiments of the above even when not initially claimed in such combinations. A teaching that two elements are combined in a claimed combination is further to be understood as also allowing for a claimed combination in which the two elements are not combined with each other, but may be used alone or combined in other combinations. The excision of any illustrated embodiment of the element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense, it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the embodiments.

I claim:

1. An apparatus for treating tissue comprising:
a light energy source;
a cooling source;
an L-shaped probe having a first segment and a second segment shorter in length than the first segment:
wherein the first segment includes an optical fiber;
wherein the second segment has an end piece that includes:
a frame;
a window, extending outside of the frame, and made of a light transmissive material and which window is configured to, by itself, deform the tissue and to transmit light energy through surfaces of the window to the tissue;
a sensor in the frame, wherein the sensor is positioned outside of an area between the window and the tissue, wherein the sensor is configured to measure a parameter of at least one of the tissue and a site adjacent to the tissue;
a prism in communication with the optical fiber;
a lens between the prism and the frame;
wherein the prism and lens are disposed entirely inside of the second segment, and which lens receives light energy from the light energy source and delivers the light energy through the window surfaces and to the tissue;
wherein the end piece communicates with cooling source; and
means for coupling the cooling source, the light energy source, and the sensor and for providing a selectively controlled heating and cooling to the tissue.

2. The apparatus of claim 1 wherein:
the tissue includes a nasal septum; and
the end piece is configured to heat selected tissue portions, while simultaneously cooling other tissue portions to avoid or minimize tissue damage.

3. The apparatus of claim 2 wherein:
the probe is multisided for insertion into each nasal fossa,
the probe further comprises two corresponding arms, each configured to different sides of the nasal septum,
one of the two corresponding arms is configured to contact one side of the nasal septum opposite another side of the nasal septum to be treated and includes means for cooling the one side to a temperature below ambient or body temperature.

4. The apparatus of claim 3 wherein:
wherein one arm includes a means for selectively heating the tissue to be treated and wherein the other arm includes a means for selectively cooling tissues adjacent to the tissue to be treated.

5. The apparatus of claim 3 wherein:
wherein one arm includes a means for selectively heating and for selectively cooling the tissue to be treated and wherein the other arm includes a means for selectively cooling tissues adjacent to the tissue to be treated.

6. The apparatus of claim 3 wherein:
wherein each arm includes means for selectively heating and for selectively cooling the tissue to be treated or the tissues adjacent to the tissue to be treated, depending on which arm is proximate to which tissue.

7. The apparatus of claim 1 wherein:
the apparatus is used to selectively deform, heat and/or cool trachea, ear, larynx, skin, fat, muscle, or cartilage.

8. The apparatus of claim 1 further comprising:
a heat sink to cool tissue using heat exchange materials, chilled water flow, thermoelectric cooling, coolant circulation, or cryogen spray.

9. The apparatus of claim 1 further comprising:
a means for precooling the probe prior to insertion of the probe into the nose or other body orifice.

10. The apparatus of claim 9 wherein:
the means for precooling the probe cools the probe to a temperature dependent upon a heat capacity of the probe, a thickness of the tissue subject to mediation, a mode or method of heat generation in the tissue or in adjacent tissues which are heated, a rate of heat generation in the adjacent tissues, and a rate of cooling of the probe during mediation.

11. The apparatus of claim 1 wherein:
the cooling source and light energy source are automatically controlled by the microprocessor controller.

12. The apparatus of claim 1 wherein:
the window is configured to apply a mechanical deformation before or after cooling of the tissue.

13. The apparatus of claim 1 wherein:
the apparatus is used for otorhinolaryngology, orthopedics, plastic surgery, general surgery, dermatology, and septoplasty operations.

* * * * *